United States Patent [19]

Bowman et al.

[11] Patent Number: 4,741,343
[45] Date of Patent: May 3, 1988

[54] METHOD AND APPARATUS FOR MEASURING OXYGEN PARTIAL PRESSURE AND TEMPERATURE IN LIVING TISSUE

[75] Inventors: H. Frederick Bowman, Needham, Mass.; Stephen K. Burns, Henniker, N.H.; David J. Edell, Lexington; James C. Weaver, Sudbury, both of Mass.

[73] Assignee: Massachusetts Institute of Technology, Cambridge, Mass.

[21] Appl. No.: 945,120

[22] Filed: Dec. 22, 1986

Related U.S. Application Data

[63] Continuation of Ser. No. 730,614, May 6, 1985, abandoned.

[51] Int. Cl.$^4$ ............................................. A61N 1/40
[52] U.S. Cl. ..................................... 128/635; 204/403; 204/408
[58] Field of Search ............... 128/630, 632, 634, 635, 128/673, 734, 736, 670; 204/403, 408

[56] References Cited

U.S. PATENT DOCUMENTS

| | | | |
|---|---|---|---|
| 3,900,382 | 8/1975 | Brown | 128/635 |
| 3,905,888 | 9/1975 | Mindt et al. | 128/635 |
| 4,120,770 | 10/1978 | Kessler | 128/635 |
| 4,197,853 | 4/1980 | Parker | 128/635 |
| 4,269,684 | 5/1981 | Zick | 128/635 |
| 4,334,541 | 6/1982 | Loist et al. | 128/635 |
| 4,375,220 | 3/1983 | Matvios | 128/401 |
| 4,461,304 | 7/1984 | Kuperstein | 128/642 |

Primary Examiner—Edward M. Coven
Attorney, Agent, or Firm—Paul J. Cook

[57] ABSTRACT

Oxygen partial pressure and temperature are measured in living tissue by inserting a thin probe into living tissue. The probe includes a plurality of spatially separated thermal sensors secured to the probe substrate. A plurality of oxygen sensors is positioned along the length of the probe substrate and each oxygen sensor is associated with and positioned adjacent to or is an integral part of one of the thermal sensors. Electrical parameters of the sensors located on the probe are measured and used to determine oxygen partial pressure and to determine temperature at each of a plurality of sites along the probe.

7 Claims, 3 Drawing Sheets

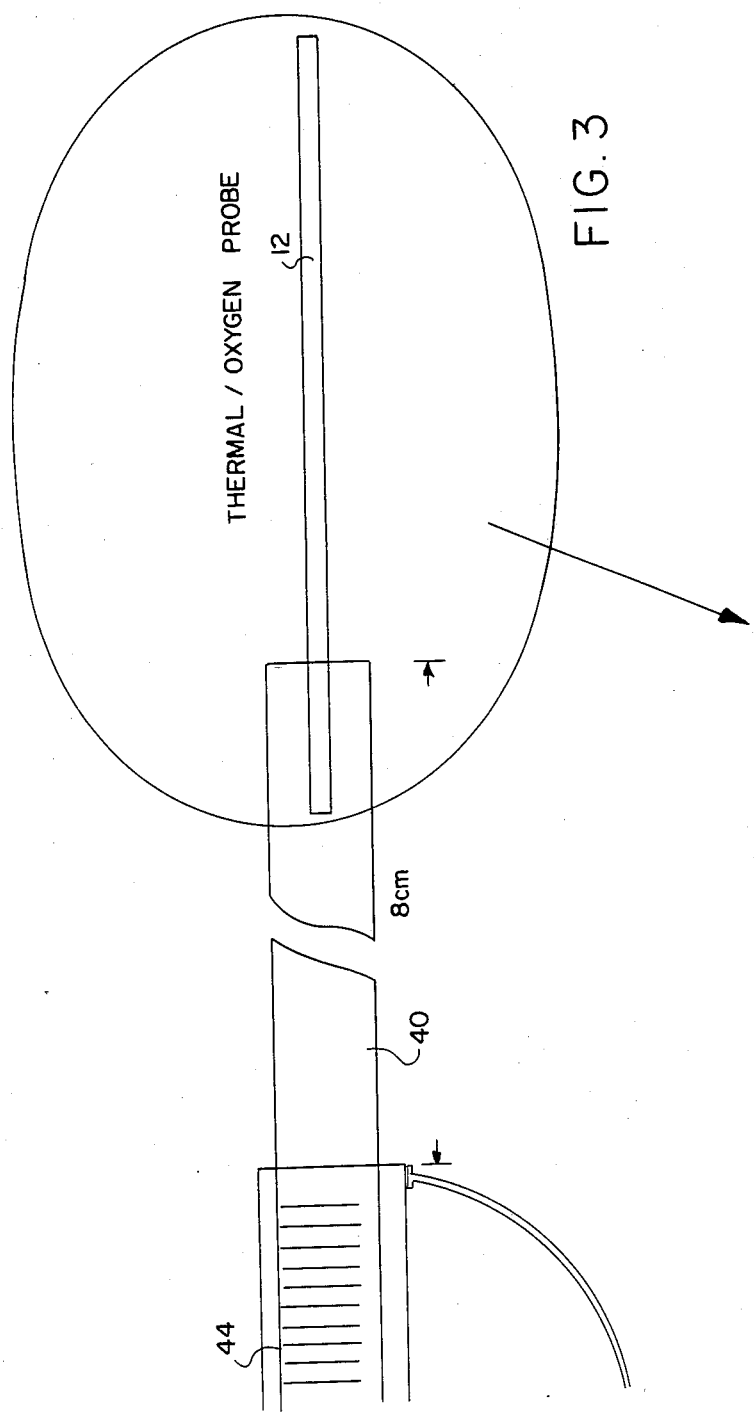
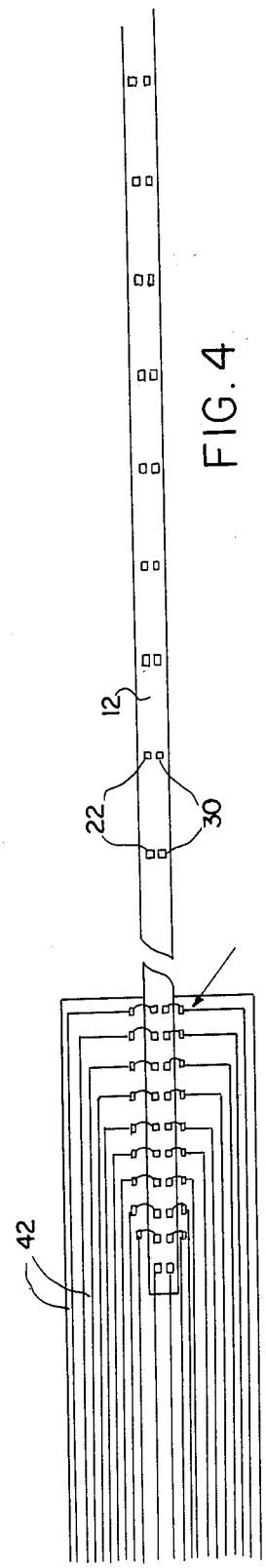
FIG. 3
FIG. 4

METHOD AND APPARATUS FOR MEASURING OXYGEN PARTIAL PRESSURE AND TEMPERATURE IN LIVING TISSUE

This is a continuation of co-pending application Ser. No. 730,614, filed on May 6, 1985, now abandoned.

BACKGROUND OF THE INVENTION

This invention relates to a method and apparatus for determining oxygen partial pressure ($PO_2$ and temperature simultaneously in living tissue at multiple sites of the tissue. More particularly, this invention relates to such an apparatus which can also determine thermal conductivity, thermal diffusivity, SAR (Specific Absorption Rate), and blood perfusion in the living tissue at multiple sites.

Interest in the fundamental mechanisms of heat transfer in living tissue and in accurate clinical thermometry derives from the face that many patients with malignancies who failed surgery, radiation, and/or chemotherapy are responsive to the local application of heat resulting in elevated tumor temperatures. Well-managed clinical application of hyperthermia requires the ability to produce specific, well-characterized temperature elevations in precisely selected volumes of tissue that comprise the malignancy. The corresponding engineering requirement is the ability to control the temporal and spatial characteristics of the absorbed thermal dose so as to produce the desired temperature distribution for the specific malignancy being treated.

The achievement and accurate measurement of the elevated temperature distribution is thus of primary importance in any hyperthermia system. The existence of computerized axial tomography makes three-dimensional visualization of tissue densities possible, and contrast angiography can also be used to map the vasculature in the tissue volume. However, neither produces temperature or oxygen images. In terms of hyperthermia heating means, microwave, radio-frequency currents, and ultrasound have been used as non-invasive sources of volumetric heat generation in tissue. Each of these three heat source means has specific advantages and limitations. An ideal system would provide control of the temporal and spatial characteristics of the heat source in order to shape the volumetric power deposition pattern to the specific requirements of the tumor mass.

In view of the rather significant tissue temperature gradients that can exist as a consequence of differential blood flow and thermal conductivity (both of which are enhanced with increased perfusion in surrounding tissue) and the clear evidence that even a small difference in temperature level could be crucial to the success of hyperthermia, it is equally crucial that good thermometry be available. Since the temperature gradient will be largest at boundaries of differential energy absorption, perfusion, and/or conductivity, it is important that the temperature at the tumor margin or proliferating edge be known. It could well be that the apparent resistance of some tumor peripheries to hyperthermia is really due to inadvertent sublethal heating due to lack of adequate thermometry at the tumor boundaries. It is the lowest temperature in the tumor and the highest temperature in the normal tissue that is limiting in the management of tumors by hyperthermia.

The state of tissue perfusion is a primary factor in the local transport of heat, the regulation of which is clearly crucial for hyperthermia; of drugs, the delivery of which is crucial in chemotherapy; and of oxygen and nutrients which are known to be important for effective radiation therapy. Thus, optimization of each of these individual cancer therapies (or synergism through combined use) each requires knowledge of the distribution and magnitude of the local level of perfusion. Differences in perfusion rates between the core and periphery of rapidly growing tumors have been found using a number of techniques, including the embedded thermistor probe (Holmes, et al., ASME *Advances in Bioengineering*, pp. 147-149, 1979). Because blood flow is known to have a dramatic influence on the temperature distribution in tissue during hyperthermia, knowledge of the magnitude and the distribution of perfusion in both the tumor and surrounding host tissue is necessary for accurate thermal therapy planning and for directing the local deposition of heat to produce uniform temperature elevations over the desired region.

There also appear to be a few important differences between blood flow in tumor and normal tissue which include: the character and distribution of the vasculature, as well as the ability to increase local perfusion in response to thermal stress at various levels and durations of local hyperthermia. Normal tissue such as skin can increase blood supply as much as seven times in response to elevated temperature of 42°-43° C. This responsive cooling mechanism has been observed as reductions in measured temperatures during hyperthermia and must be taken into account when calculating local power requirements.

It would be desirable to monitor temperature distributions accurately during hyperthermic treatments of cancer while minimally perturbing the local thermal environment. Furthermore, it would be desirable to provide a means for obtaining these measurements at a plurality of tissue locations as well as other measurements of tissue characteristic including blood perfusion, thermal conductivity, and thermal diffusivity.

In addition, determination of the spatial distribution of $PO_2$ in ionizing radiation therapy of tumors is important. Regions of tumors with low $PO_2$ do not respond adequately to ionizing radiation therapy. Therefore, direct assessment of the spatial distribution of $PO_2$ in tumors is useful in establishing whether or not radiation therapy will be successful or whether combined radiation/hyperthermia therapy will be needed. In order to be accurate, $PO_2$ measurements at multiple sites must be temperature compensated, thereby requiring a temperature measurement at each site.

SUMMARY OF THE INVENTION

In accordance with this invention, a probe adapted for insertion in living tissue is provided, which contains a plurality of thermal sensors and a plurality of oxygen sensors. Each of the oxygen sensors is positioned adjacent to a thermal sensor, and all of the sensors are connected by electrically conducting paths to means for correlating electrical currents or voltages to oxygen partial pressure and/or temperature. The electrically conducting paths also are adapted to pass current from an electrical generating source to each of the thermal sensors and means provided for measuring the electrical power needed to maintain the thermal sensors at a prescribed temperature. This power then is correlated with thermal conductivity, thermal diffusivity, blood perfusion, and specific thermal absorption rate of the tissue surrounding the probe. The apparatus of this invention can be operated in alternating modes wherein electrical current generated by the oxygen sensors and thermal sensors are measured or wherein rate of currents applied to the thermal sensors is measured. By operating in this alternating mode, at least six characteristics of the tissue surrounding the probe can be measured; namely oxygen partial pressure ($PO_2$), temperature, thermal conductivity, thermal diffusivity, blood perfusion, and specific thermal absorption rate.

BRIEF DESCRIPTION OF THE DRAWINGS

FIG. 3 is a top view of the probe of this invention.

FIG. 4 is a more detailed view of the probe shown in FIG. 3.

DESCRIPTION OF SPECIFIC EMBODIMENTS

Figure 2:
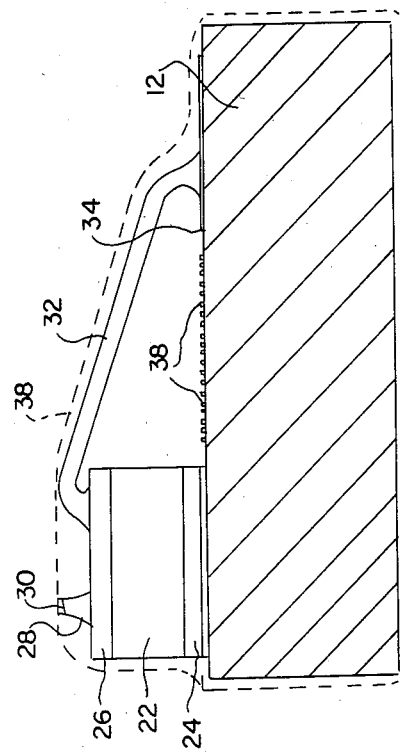
FIG. 2 is a cross sectional view of one embodiment of the probe of this invention.

In accordance with this invention, an apparatus is provided which includes a probe substrate having a diameter sufficiently small so that it can be inserted into living tissue, more specifically tumor tissue. The size of the probe substrate, including its length and cross section, are arbitrary. The practical substrate cross-sectional dimension will be between 100 and 1,000 microns, and the length will be between 0.5 and 20 centimeters. Materials are selected and the probe arrays are designed to provide a good thermal match to tissue. Thermal sensors are secured to the probe substrate such as by bonding, soldering, or polymeric adhesives and are spaced apart, uniformly or nonuniformly as desired, along the probe substrate along the length of the probe substrate to provide a plurality of positions wherein tissue temperature can be measured at each position. Representative suitable thermal sensor include thermistors, diodes, or other P-N junctions. Thermocouples may be used as temperature sensors at the expense of being able to obtain thermal property and derived perfusion measurements. A preferred thermal sensor is a thermistor including an exposed surface formed of a noble metal such as gold and wherein an electrically conductive path is provided from the noble metal portion of the thermistor to a thin electrically conductive path that extends along the length of the probe substrate to a point outside of the living tissue.

A plurality of oxygen sensors is also provided. Each of the oxygen sensors is positioned either very closely, within 100 μm of less, to a single thermal sensor or is an integral part of a thermal sensor or on the thermal sensor. The purpose of positioning the oxygen sensor close to a thermal sensor is that an oxygen sensor is significantly temperature sensitive. Further, oxygen partial pressure in tissue is also temperature dependent, so that in order to determine actual oxygen partial pressure, it is necessary that the temperature at the measurement site be known with sufficient accuracy, viz. ±0.01° C. Thus, the measurement of temperature at each of the thermal sensor locations not only provides a temperature measurement, but provides a means whereby a suitably corrected oxygen partial pressure measurement can be obtained at each location of the oxygen sensors. Each of the oxygen sensors is also connected to a thin electrically conductive path which leads to a point outside the living tissue to means which correlate the electrical current flowing through each oxygen sensor with the oxygen partial pressure. Each thermal sensor also is connected to a means located outside the living tissue which correlates the potential measured across the thermistor created by a known current flow with tissue temperature. At each site an oxygen measurement is made using one lead and a reference electrode remotely located elsewhere in the tissue. The temperature measurement is made using the other lead of the pair with the oxygen lead and reference electrode connected to reference potential.

It is to be noted that, in one embodiment of this invention, it is not necessary that all of the thermal sensors have an oxygen sensor associated therewith. It is only necessary that a sufficient number of oxygen sensors, each associated with a thermal sensor, are provided so that oxygen partial pressure measurements can be obtained at a suitable number of sites within the tissue of interest. This is primarily of interest in cancerous tumor tissue or tissue study or assessment wherein it is necessary to know the oxygen partial pressure within the tissue. For example, in radiation therapy the presence of oxygen in the tissue being radiated is necessary in order to render the radiation effective in killing the cancerous tumor tissue. If a diagnostician determines that there is insufficient oxygen present in the tissue to render radiation therapy effective, then alternative forms of therapy can be utilized. Since cancerous tumors vary widely in size, the number and spatial separation of oxygen sensors along the probe substrate also will vary accordingly. Generally, it is necessary to utilize at least two oxygen sensors, preferably between about five and about 20 oxygen sensors up to about 100 oxygen sensors spaced apart along the surface of the probe substrate. As noted above, each oxygen sensors must have associated with it a thermal sensor so that the oxygen partial pressure measurement obtained can be adjusted to account for the effect of temperature in the tissue surrounding the oxygen sensor.

Each oxygen and thermal sensor pair is connected to a means located outside the living tissue which translates the electrical currents and resistance to the desired physical parameters of oxygen concentration, temperature, and derived quantities. The electrical connection is provided by a single pair of leads (or optionally a single lead and a common connection to other combined sensors). By sensing the low-frequency direct current developed by the oxygen sensor in combination with an indifferent common located elsewhere within the conducting tissue, and the high frequency signal developed across the thermal electrode, both parameters can be simultaneously measured. The thermal electrode can be optionally heated by using a larger high frequency excitation which results in appreciable resistive heating. Separation of signals is achieved by virtue of the differing frequencies of the oxygen and the temperature information. As an alternative method of accessing the information provided by a multiplicity of sensors which share common leads, a sequence of excitations and interrogations can be provided and the results stored in the memory of a microprocessor which can then derive the desired information.

The electrically conducting path connected to the oxygen sensors and the thermal sensors pass along the probe substrate out of the tissue and are connected with means adapted to convert the electrical signals to oxygen partial pressure and temperature. Any conventional microprocessor, computer, analog circuit, computational device, table, or the like can be utilized so long as it is programmed by means well known in the art to convert the electrical current measurements to oxygen partial pressure and temperature by taking into account the following parameters: oxygen electrode polarization potential, temperature of oxygen interface, oxygen electrode current, diffusion coefficient of oxygen in gradient near electrode, geometry of oxygen electrode, lead resistance, lead temperature-resistance relationship, lead temperature (computed from thermistor measurements), thermistor resistance, thermistor temperature-resistance relationship, characteristic thermistor dimension, and power-time relationship of heated sensors. By providing an accurate measurement of oxygen partial pressure as a function of tissue location, which takes into account the effect of temperature, the person skilled in the art can, for the first time, utilize this miniature, minimally invasive means for determining whether therapeutic procedures, which rely upon the presence of oxygen in the tumor tissue, can be employed satisfactorily. Furthermore, since the apparatus of this invention provides accurate temperature measurement at distinctive separate locations within the tissue where the probe substrate is inserted, one can determine whether all or only a portion of tumor tissue being heat irradiated has achieved a sufficiently high temperature to be effective to kill the tumor tissue. As noted above, if a minimum temperature, usually between about 42.5° and 44° C., is not achieved continuously over the therapy time period, usually between about 20 and about 40 minutes, then therapy will be ineffective since only a portion of the tumor tissue will be killed. If this occurs, the remaining living cells will continue to multiply rendering the therapy ineffective. Thus, the present invention provides a means whereby heat radiation therapy of tumor tissue can be evaluated on a more local basis for efficacy. Such assessment will not be based on large average temperature measurements, but by distinct and separate temperature measurements showing the specific time-temperature conditions under which heat radiation therapy is or is not effective. When the measurement shows the therapy to be ineffective, the temperature of the therapy is raised and the radiation is directed to portions of the tumor according to the measurements.

The apparatus of this invention also can be utilized to provide measurements of the characteristics of the tissue surrounding the probe substrate such as thermal conductivity, thermal diffusivity, blood perfusion, and/or specific thermal absorption rate. Electrical power is supplied to the thermal sensor. The power input to the thermal sensor is regulated by any conventional means such as an electronic control circuit so that a predetermined mean temperature is reached rapidly and is maintained at the desired constant level above a reference temperature. Any variations in the desired temperature level are appropriately sensed so that the controller can then increase or reduce the input power to the thermal sensor to a value which maintains the temperature thereof at a desired level. A variable voltage, which is applied to the thermal sensor, can be converted to digital form and can be used as digital input information to a data processor which is arranged to calculate thermal conductivity, thermal diffusivity, perfusion, and specific thermal absorption rates. The means for determining thermal conductivity and thermal diffusivity are disclosed, for example, in U.S. Pat. No. 4,059,982, which is incorporated herein by reference. Perfusion can be calculated by any means well known in the art as those based on the bioheat equation or simplifications thereof. Example being taught in U.S. Pat. No. 4,059,982. The specific thermal absorption rate (SAR) or local deposition of energy can be determined from the initial slope of the temperature-time curve modified by multiplying the product of tissue density $\rho$ and heat capacity c. The product $\rho c$ is known from the ratio of thermal conductivity k to thermal diffusivity $\alpha$; $\rho c = k/\alpha$.

Figure 1:
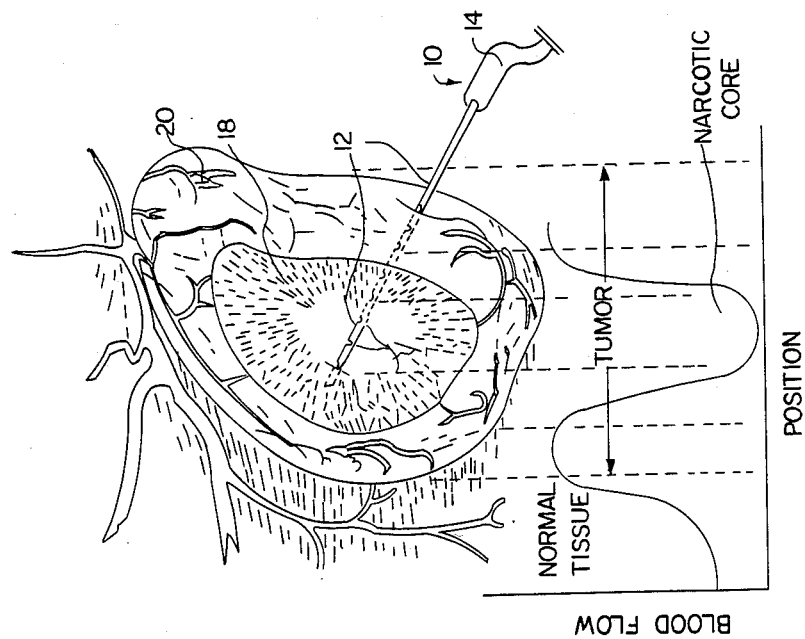
FIG. 1 is a cross sectional view of a tumor tissue having the probe of this invention inserted therein and representative blood flow as a function of tissue position.

Referring to FIG. 1, the apparatus of this invention 10 includes a probe substrate 12 and a handle 14 attached to the probe substrate 12 and through which conductive paths can be made for connection with electrical current processing means (not shown). The thermal probe includes a plurality of sensor sites 16, each of which sensor sites includes a thermal sensor and an oxygen sensor. The tissue into which the probe substrate 12 extends includes tumor tissue 18 and normal tissue 20. As shown in FIG. 1, blood flow through the normal tissue 20 and the tumor tissue 18 varies with position. Therefore, oxygen partial pressure, temperature, thermal conductivity, thermal diffusivity, blood perfusion, and specific thermal absorption rate within the tissue 18 and 20 will vary with position.

As shown in FIG. 2, the probe substrate 12 had bonded thereto a thermistor 22 which is coated with a noble metal such as gold 24 and 26. An oxygen sensor 28 is provided which is coated with a noble metal such as gold or platinum 30. The thermistor 22 is bonded to the prob substrate 12. A conducting wire 32 is also bonded to probe substrate 12 and provides a conductive path from the thermistor 22 to a second conductive path 34, which second conductive path extends along the probe substrate 12 and out of the tissue to the electrical processing apparatus (not shown). A plurality of conductive paths 28 represents conductive paths from upstream oxygen sensors and thermal sensors (not shown). The entire oxygen sensor-thermal sensor-connecting wires and probe substrate can be enclosed with an insulating material such as polyimide or epoxy resin 38 or other coatings with insulating properties, so long as the normal metal portion of the oxygen sensor 30 is not enclosed by the insulating material. As shown in FIGS. 3 and 4, the probe substrate 12 includes a plurality of thermal sensors 22 and a plurality of oxygen sensors 30 which are attached to a polymer ribbon cable 40 which includes a plurality of conductive paths 42 that are connected with an edge connector 44 which, in turn, is connected to an electronic processing means or the like (not shown).

Figure 5:
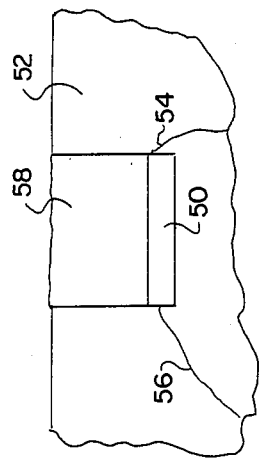
FIG. 5 shows a cross sectional view of an oxygen sensor surrounded by a gel matrix.
Figure 6:
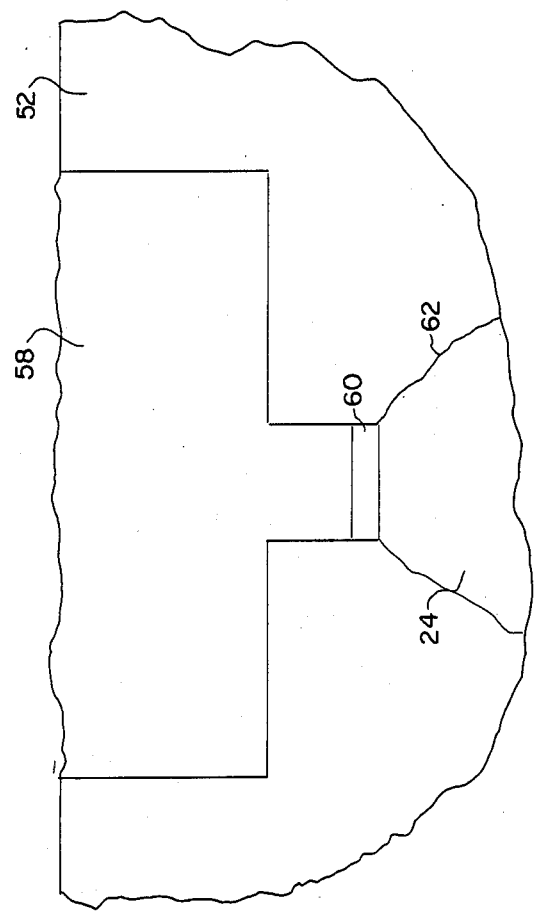
FIG. 6 is a cross sectional view of an alternative oxygen sensor of this invention surrounded by a gel matrix.

Referring to FIG. 5, in one embodiment the oxygen sensor 50 can be formed within the thermal probe 52 and can be connected with conducting paths 54 and 56. A gel medium 58 of known oxygen diffusivity is provided to protect the oxygen sensor 50 and to provide a medium of known oxygen diffusivity. Since oxygen diffusivity varies from tissue to tissue, this oxygen sensor structure can be more easily calibrated to determine actual oxygen diffusivity through tissue adjacent the gel 58. More accurate calibration can be obtained with the apparatus shown in FIG. 6 which includes the oxygen sensor 60 connecting conductive paths 62 and 64, probe substrate 52 and gel 58. The increased volume of gel reduces the effect of varying oxygen diffusivity through adjoining tissue and provides a gel medium wherein oxygen diffusivity can be accurately determined within 99% of actual diffusivity or better.

We claim:

1. Apparatus for measuring at least one characteristic of living tissue comprising oxygen partial pressure, temperature, thermal conductivity, thermal diffusivity, specific absorption rate, and perfusion in living tissue at a plurality of locations in said tissue, which comprises a thin probe substrate having a cross-section sufficiently small to permit insertion of said thin probe into said tissue, a plurality of thermal sensors secured spatially separated sites along the length of said probe substrate, a plurality of oxygen sensors positioned at spatially separated sites along the length of said probe substrate, means for polarizing said oxygen sensors, each of said oxygen sensors being positioed within 100 $\mu$m or less or comprises a portion of one of said thermal sensors, each of said oxygen sensors and said thermal sensors being sufficiently small to permit insertion of said thin probe, said oxygen sensors and said thermal sensors into said tissue, electrical connecting means for supplying known electrical excitation to each of said thermal sensors, said thermal sensors having electrical resistance means for sensing electrical resistance of said thermal sensors means for sensing the direct current produced by said oxygen sensors when said oxygen sensors are polarized and means for converting said resistance and said direct current to said at least one characteristic.

2. The apparatus of claim 1 wherein an oxygen sensor is positioned adjacent each thermal sensor.

3. The apparatus of claim 1 or 2 wherein the number of thermal sensors and the number of oxygen sensors is between two and 100.

4. The apparatus of claim 1 or 2 wherein said oxygen sensors are recessed within said substrate and a gel of known oxygen diffusivity and thermal conductivity is positioned between said oxygen sensors and tissue nearest said gel.

5. The process of determining oxygen partial pressure and temperature at a plurality of locations within living tissue which comprises inserting into said tissue the probe substrate of the apparatus of claim 1, measuring current electrical parameters associated with each oxygen and thermal sensor and determining by said electrical parameters the oxygen partial pressure and temperature at each of said locations.

6. The process of determining at least one derived parameter of a living tissue characteristic selected from the group consisting of thermal conductivity, thermal diffusivity, blood perfusion, and specific thermal absorption rate which comprises inserting into said tissue the probe of claim 1, supplying electrical power to each of said thermal sensors, measuring the rate of power supplied to maintain said thermal sensors at a known temperature and correlating the rate of power supplied to at least one derived parameter.

7. The process of alternately determining (a) oxygen partial pressure and temperature at a plurality of locations within living tissue and (b) at least one derived parameter of living tissue characteristic comprising thermal conductivity, thermal diffusivity, blood perfusion, and specific thermal absorption rate which comprises (c) inserting into said tissue the probe of claim 1 and, when measuring (a), measuring electrical parameters associated with each of said oxygen sensors and electrical parameters associated with each thermal sensor and correlating said parameters to oxygen partial pressure and said parameters to temperature at each of said locations and (d) when measuring (b), measuring the rate of power supplied to maintain said thermal sensors at a known temperature and correlating the rate of power supplied to said at least one derived parameter.

* * * * *